(12) United States Patent
Wollin (10) Patent No.: US 10,502,602 B2
(45) Date of Patent: Dec. 10, 2019

(54) APPARATUS AND METHOD FOR MEASURING VELOCITY AND COMPOSITION OF MATERIAL IN AND ADJACENT TO A BOREHOLE

(71) Applicant: Wollin Ventures, Inc., Sarasota, FL (US)

(72) Inventor: Ernest Wollin, Sarasota, FL (US)

(73) Assignee: WOLLIN VENTURES, INC., Sarasota, FL (US)

(*) Notice: Subject to any disclaimer, the term of this patent is extended or adjusted under 35 U.S.C. 154(b) by 400 days.

(21) Appl. No.: 14/874,835

(22) Filed: Oct. 5, 2015

(65) Prior Publication Data
US 2016/0097664 A1 Apr. 7, 2016

Related U.S. Application Data

(60) Provisional application No. 62/060,321, filed on Oct. 6, 2014.

(51) Int. Cl.
| | |
|---|---|
| *G01F 1/716* | (2006.01) |
| *E21B 47/10* | (2012.01) |
| *G01N 24/08* | (2006.01) |
| *G01R 33/38* | (2006.01) |
| *G01R 33/483* | (2006.01) |
| *G01R 33/34* | (2006.01) |
| *G01R 33/381* | (2006.01) |
| *G01R 33/383* | (2006.01) |

(52) U.S. Cl.
CPC ........... *G01F 1/716* (2013.01); *E21B 47/10* (2013.01); *G01N 24/081* (2013.01); *G01R 33/3808* (2013.01); *G01R 33/4835* (2013.01); *G01R 33/34076* (2013.01); *G01R 33/381* (2013.01); *G01R 33/383* (2013.01)

(58) Field of Classification Search
None
See application file for complete search history.

(56) References Cited

U.S. PATENT DOCUMENTS

| | | |
|---|---|---|
| 4,782,295 A | 11/1988 | Lew |
| 5,532,593 A | 7/1996 | Maneval et al. |
(Continued)

OTHER PUBLICATIONS

Balanis, C.A. "Advanced Engineering Electromagnetics", John Wiley & Sons, 1989, pp. 72-103.
(Continued)

*Primary Examiner* — Jermele M Hollington
*Assistant Examiner* — Suresh K Rajaputra
(74) *Attorney, Agent, or Firm* — Foley & Lardner LLP (57) ABSTRACT

This disclosure provides systems, methods, and apparatus for measuring flow in and around a borehole of an earth formation. A flow measurement device can include a magnet configured to generate a static solenoidal magnetic field with a field intensity that decreases in strength peripherally from the magnet, an electromagnet disposed around the magnet and configured to generate a time varying solenoidal magnetic field, and a radio frequency (RF) coil disposed around the magnet and configured to generate an RF magnetic field transverse to the static solenoidal magnetic field. The flow measurement device can calculate a flow velocity in and around the flow measurement device based upon a signal received by the RF coil.

20 Claims, 3 Drawing Sheets

(56) References Cited

U.S. PATENT DOCUMENTS

| | | | | |
|---|---|---|---|---|
| 5,604,891 | A | * | 2/1997 | Burnett ............... G06F 17/5018 345/419 |
| 6,166,540 | A | | 12/2000 | Wollin |
| 6,452,390 | B1 | * | 9/2002 | Wollin .................... G01F 1/716 324/306 |
| 2006/0020403 | A1 | * | 1/2006 | Pusiol .................... G01F 1/716 702/45 |
| 2008/0174309 | A1 | * | 7/2008 | Pusiol ....................... G01F 1/56 324/306 |
| 2009/0251145 | A1 | * | 10/2009 | Kaneko ............ G01R 33/34046 324/318 |
| 2013/0181706 | A1 | * | 7/2013 | Blanz ....................... G01V 3/32 324/303 |

OTHER PUBLICATIONS

Cho, Z. et al. "Foundations of Medical Imaging". John Wiley & Sons, Inc., New York, 1993, pp. 374-386.

Den Hartog, J.P. "Mechanics". McGraw Hill Book Co., 1948.; Dover Publications Inc. 1961, pp. 313-340.

Mansfield, P, et al. "NMR Imaging in Biomedicine"; Advances in Magnetic Resonance, Supplement 2; 1982; Academic Press, Inc., Orlando, pp. 234-239.

Poularikas, A.D., Ed. "The Transforms and Applications Handbook," CRC Press, 1996, pp. 221-222.

Slichter, C.P. "Principles of Magnetic Resonance". Third Edition, Springer-Verlog, 1989, Ch. 2, pp. 11-64.

Smythe, W.R. "Static and Dynamic Electricity". Second Edition. McGraw Hill Book Co, 1950, pp. 390-397.

Non-Final Office Action issued in U.S. Appl. No. 16/575,230 dated Oct. 21, 2019 and US 2003/0071617 cited therein.

* cited by examiner

APPARATUS AND METHOD FOR MEASURING VELOCITY AND COMPOSITION OF MATERIAL IN AND ADJACENT TO A BOREHOLE

RELATED APPLICATIONS

This application claims benefit under 35 U.S.C. § 119(e) of Provisional Application Ser. No. 62/060,321, filed Oct. 6, 2014, entitled "Apparatus and Method for Measuring Velocity and Composition of Material in and Adjacent to a Borehole."

BACKGROUND OF THE INVENTION

1. Field of the Invention

This disclosure relates to the field of flow measurement, and in particular to apparatus and processes for measuring flow using nuclear or electron magnetic resonance.

2. Description of the Prior Art

The idea of studying flow by magnetic resonance dates back to the work of the early pioneers as described, for example, in Mansfield, P; Morris, P. G.; "NMR Imaging in Biomedicine"; Advances in Magnetic Resonance, Supplement 2; 1982; Academic Press, Inc. Orlando 32887; p. 235 section 7.3.5. Prior art devices for flow measurement or flow mapping rely on two well-known methods viz. "Time-of-Flight" of saturated or unsaturated spins or "Phase-Encoding" by application of a gradient field along the direction of flow. (Cho, Z. et. al.; "Foundations of Medical Imaging;" John Wiley & Sons, Inc., New York, 1993, p 374-386.) Exemplary of the "Time-of-Flight" method is U.S. Pat. No. 4,782,295 to Lew and of the "Phase-Encoding" method is U.S. Pat. No. 5,532,593 to Maneval. Analysis of chemical composition by chemical shift is discussed in "Principles of Magnetic Resonance," third edition chapter 4, by Slichter, C. P., Springer-Verlag, N. Y. 1989. The nuclear Overhauser effect is discussed in chapter 7.

Those prior art methods employ pulse techniques that broaden the bandwidth thereby increasing the noise in the measurement signal. A departure from this prior technology is the quasi-steady-state technique in U.S. Pat. No. 6,452,390, incorporated by reference herein for all purposes, in which simultaneous spatial and temporal nutation and phase encoding of the moving spins permit simultaneous reception of the measurement signal in the continuous presence of the adjustable Larmor frequency excitation field. The quasi-steady-state condition creates a minimal bandwidth, limiting the Johnson Nyquist noise in the received measurement signal. Further, prior art methods pertain to measurements within a conduit and not to measurements around the device where there may be a strong component of velocity peripheral to the device.

SUMMARY

The systems, methods and devices of this disclosure each have several innovative aspects, no single one of which is solely responsible for the desirable attributes disclosed herein.

One innovative aspect of the subject matter described in this disclosure can be implemented in a flow measurement device for measuring flow in or around a borehole of an earth formation. The flow measurement device can include a magnet configured to generate a static solenoidal magnetic field with a field intensity that decreases in strength peripherally from the magnet. The flow measurement device can include an electromagnet disposed around the magnet and configured to generate a time varying solenoidal magnetic field. The flow measurement device can include a radio frequency (RF) coil disposed around the magnet. The RF coil can be configured to generate an RF magnetic field transverse to the static solenoidal magnetic field and rotating at the Larmor radio frequency corresponding to the field intensity in a region of interest around the flow measurement device. The RF coil can be configured to output a received signal, the received signal induced by a magnetic field around the RF coil.

In some implementations, the electromagnet is a helical coil disposed around the magnet. In some implementations, the RF coil can comprise a birdcage coil disposed around the magnet. In some implementations, the RF coil can comprise a first birdcage coil disposed around the magnet and configured to operate at a first frequency, and a second birdcage coil disposed around the magnet and configured to operate at a second frequency. In some implementations, the RF coil can comprise a transmitting birdcage coil disposed around the magnet and configured to generate the RF magnetic field, and a receiving birdcage coil disposed around the magnet and configured to output the received signal. In some implementations, the RF coil can comprise a quadrature coil. In some implementations, the region of interest around the flow measurement device is a surface of a prolate or oblate spheroid having a finite thickness.

In some implementations, the flow measurement device can include a controller configured to calculate a flow velocity through the region of interest around the flow measurement device based on the received signal. In some implementations, the controller can be configured to select the Larmor frequency to correspond to the region of interest around the flow measurement device, adjust a magnitude of a time varying current applied to the electromagnet to maximize a magnitude of a first side band of the received signal, and adjust a magnitude of an RF current applied to the RF coil to maximize the received signal. In some implementations, the controller can be configured to calculate a mean dwell time of spins in the region of interest around the flow measurement device based on the magnitude of the RF current applied to the RF coil, and calculate the flow velocity through the region of interest around the flow measurement device based on the received signal.

Another innovative aspect of the subject matter described in this disclosure can be implemented in a method of measuring flow in or around a borehole in an earth formation. The method can include inserting a flow measurement device into the borehole in the earth formation, the flow measurement device comprising a magnet, an electromagnet disposed around the magnet, and a radio frequency (RF) coil disposed around the magnet. The method can include generating, using the magnet, a static solenoidal magnetic field, wherein the static solenoidal magnetic field has a field intensity that decreases in strength peripherally from the magnet. The method can include generating, using the electromagnet, a time varying solenoidal magnetic field. The method can include generating, using the RF coil, an RF magnetic field transverse to the static solenoidal magnetic field and rotating at a Larmor radio frequency corresponding to the field intensity in a region of interest around the flow measurement device. The method can include receiving a received signal induced in the RF coil by a magnetic field around the RF coil.

In some implementations, the method can include calculating a flow velocity through the region of interest around the flow measurement device based on the received signal.

In some implementations, the method can include selecting the Larmor frequency to correspond to the region of interest around the flow measurement device, adjusting a magnitude of a time varying current applied to the electromagnet to maximize a magnitude of a first side band of the received signal, and adjusting a magnitude of an RF current applied to the RF coil to maximize the received signal. In some implementations, the method can include calculating a mean dwell time of spins in the region of interest around the flow measurement device based on the magnitude of the RF current applied to the RF coil, and calculating the flow velocity through the region of interest around the flow measurement device based on the received signal.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

Like reference numbers and designations in the various drawings indicate like elements.

DETAILED DESCRIPTION

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system that is capable of measuring velocity of flow in and around a borehole in an earth formation.

The following disclosure pertains to measuring velocity of flow and composition of material moving within a borehole or peripherally in a surrounding volume. The borehole may be present in an earth formation or a man-made structure. The borehole may contain a flow measurement device employing nuclear spin or electron spin magnetic resonance for measurement. Applications of the measurement device disclosed herein include hydrocarbon production, hydraulic fracturing, groundwater migration, contaminant diffusion, wireline logging, or detecting formation migration or tectonic plate shift.

Measurement of flow by magnetic resonance utilizing time of flight or gradient phase encoding techniques are known. Prior methods employ pulse techniques that broaden the bandwidth thereby increasing the noise in the measurement signal. A departure from this prior technology is the quasi-steady-state technique described in U.S. Pat. No. 6,452,390, incorporated by reference herein for all purposes, in which simultaneous spatial and temporal nutation and phase encoding of the moving spins permit simultaneous reception of the measurement signal in the continuous presence of the adjustable Larmor frequency excitation field. The quasi-steady-state condition creates a minimal bandwidth limiting the Johnson Nyquist noise in the received measurement signal.

The present disclosure differs from the disclosure of U.S. Pat. No. 6,452,390 in the configuration of its various field inducing components, and in its technique of flow measurement. Further, U.S. Pat. No. 6,452,390 does not disclose a method or apparatus measure or calculate the peripheral flow in an earth formation surrounding a borehole. Further, the present disclosure also differs from U.S. Pat. No. 6,166,540 (including each of its divisional and continuation applications) in the configuration of its various field inducing components, and its technique of estimating geophysical aspects of an earth formation surrounding a borehole within the earth formation.

A magnet introduced into a borehole can generate a strong magnetic field both in the borehole and in the adjacent formation. Spins migrating in this strong field acquire a magnetization by $T_1$ relaxation until they enter the region of interest at a depth of investigation selected by a radio frequency ("RF") magnetic field and acquire a transverse component of magnetization, which can induce a voltage in the receiver coil. As used herein, the depth of investigation refers to a distance to the region of interest from the center of the flow measurement device. An electromagnet adjacent to the strong magnet can produce a weaker slowly time varying component of that strong magnetic field, creating phase modulation of the spins and permitting detection in the presence of the continuous radio frequency field. Adjusting the strength of the radio frequency field for maximum received signal can yield a known function of the mean dwell time of the spins in the volume of, and at the depth of, investigation. The following background is helpful to understanding the flow measurement device described herein.

Introduction to Simultaneous Nutation and Periodic Phase Encoding of Moving Spins ("SNAPPEMS")

Transient response of spin systems have usually been described by solutions to the Bloch equations (Slichter, C. P. "Principles of Magnetic Resonance", Third Edition. Springer-Verlog 1989, op. cit., p. 33, Ch. 2) which describes the magnetization as a function of both the applied magnetic fields and the relaxation effects on a phenomenological basis. Solutions to the Bloch equations require assumptions about the magnitude of these parameters and prescription of boundary conditions, creating a differential system applicable to a particular set of circumstances. To simplify this process further, the description below begins with the equation of motion of an isolated spin, modeled as gyroscopic precession driven by moments created by applied magnetic fields, then introduces the total magnetization as a function of spin density, and finally limits the applicability of the equations so derived by the relationship between the times of the event sequence to the relaxation times.

Gyroscopic Precession

"A rigid body free in space without any constraints can rotate permanently only about a principal axis of inertia" (Den Hartog, J. P., "Mechanics". McGraw Hill Book Co., 1948. Dover Publications Inc. 1961, op. cit., p. 315 No XII). "If a rigid body rotates with speed $\omega_1$ about a principal axis of inertia, and with $\omega_2=\omega_3=0$ about the other two principal axes, then the angular momentum vector (i.e. moment of momentum vector) $\vec{M}$ has the same direction as the angular-speed vector $\omega_1$ (which is along the axis of rotation)," (Hartog, J. P., op. cit., p. 315 No VIII). "Angular velocities of a rigid body about various axes in space, all intersecting in a point, can be compounded vectorially into a resultant angular speed about THE axis of rotation" (Hartog, J. P., op. cit. p. 314 No III).

We infer from the last statement that the resultant angular speed $\omega_1$ about THE axis of rotation taken as the resultant angular velocity $\vec{\omega}$ can be decomposed into a vector sum of angular velocities $\Sigma\vec{\omega}_n$. Further, taking the rigid body as having mass symmetrically distributed about all axes through the center of mass yields a constant scalar moment of inertia $I_0$ about all axes, leading to the desired result decomposing the angular momentum vector $\vec{M}$:

$$\vec{M} = I_0\vec{\omega} = \sum_n I_0\vec{\omega}_n.$$

From Newton's equations (Hartog, J. P., op. cit., p. 277, eq. 27b), with $\vec{M}_G$ being the moment of external forces about the center of mass:

$$\vec{M}_G = \frac{d}{dt}I_0\vec{\omega} = \sum_n \frac{d}{dt}I_0\vec{\omega}_n.$$

Thus the vector sum of the moments of a set of external forces $\Sigma\vec{M}_{G_n}$ equals the time rate of change of the total angular momentum $I_0\vec{\omega}$, i.e:

$$\vec{M}_G = \sum_n \vec{M}_{Gn} = \frac{d}{dt}I_0\vec{\omega} = \sum_n \frac{d}{dt}I_0\vec{\omega}_n.$$

Gyromagnetic Ratio

Taking the rigid body as having a symmetrical distribution of charge about the center of mass creates a magnetic moment $\vec{\mu}$ about any axis of rotation proportional to the angular velocity $\vec{\omega}$ about that axis of rotation (Smythe, W. R. "Static and Dynamic Electricity", Second Edition. McGraw Hill Book Co 1950, op. cit., p. 260) where each element of charge dq at distance r from the axis of rotation creates an element $d\vec{\mu}$ of this magnetic moment $\vec{\mu}$ where, by definition of the magnetic moment, $$d\vec{\mu} = (\pi r^2)(r\vec{\omega})\frac{dq}{2\pi r}$$

(Balanis, C. A., "Advanced Engineering Electromagnetics". John Wiley and sons 1989, op. cit., p. 87, eq. 2-82).

Each element of mass dw at distance r from this axis of rotation creates an element of the angular momentum (moment of momentum) dM of (Hartog, op. cit., p. 276)

$$d\vec{M} = (r)(r\vec{\omega})dw \qquad \text{(Balanis, op. cit., p. 87, eq. 2-83)}.$$

The ratio is assumed to be a constant:

$$\frac{d\vec{\mu}}{d\vec{M}} = \frac{1}{2}\left(\frac{dq}{dw}\right) \equiv \gamma$$

(Balanis, op. cit., p. 87, eq. 2-84).

$\gamma$ being a scalar constant termed the gyromagnetic ratio.

Integrating, with boundary condition $\vec{\mu}=0$ when $\vec{M}=0$ yields:

$$\vec{\mu} = \gamma\vec{M}.$$

General Equation of Motion of an Isolated Spin

A magnetic moment $\vec{\mu}$ subjected to a field of magnetic induction $\vec{B}$ will experience a mechanical moment (torque) $\vec{M}$ such that:

$$\vec{M} = \vec{\mu} \times \vec{B} \qquad \text{(Smythe, W. R., op. cit., p. 261)}$$

In free space of permeability $\mu_0$, the magnetic induction $\vec{B}$ is proportional to the magnetic field intensity $\vec{H}$:

$$\vec{B} = \mu_0\vec{H}$$

Equating the rate of change of the angular momentum to the applied mechanical moment (torque) yields $$\vec{\mu} \times \vec{B} = \frac{d}{dt}\vec{M}$$

(Slitcher, op. cit., p. 11, eq. 2.1).

Multiplying by the gyromagnetic ratio $\gamma$ and substituting $\vec{\mu}=\gamma\vec{M}$ and $\vec{B}=\mu_0\vec{H}$ yields $$\vec{\mu} \times (\gamma\mu_0)\vec{H} = \frac{d}{dt}\vec{\mu}.$$

Defining $\gamma'=\gamma\mu_0$ yields the equation of motion of a magnetic moment (spin) subjected to a magnetic field intensity $\vec{H}$:

$$\vec{\mu} \times \gamma'\vec{H} = \frac{d}{dt}\vec{\mu}.$$

Dividing by $\mu$ yields the instantaneous angular velocity of a magnetic moment (spin) $\vec{\mu}$ subjected to a time varying ambient magnetic field intensity $\vec{H}$:

$$\vec{1}_\mu \times \gamma'\vec{H} = \frac{d}{dt}\vec{1}_\mu,$$

which is a linear differential equation with constant coefficients, allowing superposition.

Decomposing $\vec{H}$ into $H_0$, $h_p$, and $h_n$

Define an orthogonal coordinate system for $\vec{1}_\mu$ and $\vec{H}$ as $\vec{z}, \vec{x}, j\vec{y}$ where $\vec{x}+j\vec{y}$ forms Gaussian planes everywhere orthogonal to $\vec{z}$. This allows decomposition of the ambient magnetic field intensity $\vec{H}$ such that:

$$\vec{H} = [H_0 + h_p\cos(\Omega t)]\vec{z} + h_n e^{j\gamma' H_0 t},$$

where $H_0$ is a strong non-time variant ambient magnetic field intensity, $h_p$ is co-aligned with $H_0$ and sinusoidally periodic at frequency $\Omega$, and $h_n$ is everywhere orthogonal to $H_0$ rotating in the local orthogonal $\vec{x}$, $j\vec{y}$ Gaussian plane at angular velocity $\gamma'H=\gamma\mu_0H_0=\gamma B_0=\omega_0$, which is the Larmor frequency.

Equation of Motion of SNAPPEMS
Substituting and rearranging in differential form $$d\vec{T}_\mu = (\vec{T}_\mu \times \gamma'\vec{H}_0\vec{z})dt + (\vec{T}_\mu \times [\gamma'h_p\cos(\Omega t)]\vec{z})dt + (\vec{T}_\mu \times \gamma'h_n e^{j\gamma'H_0 t})dt$$

The first term creates a constant precession of $\vec{T}_\mu$ of angular velocity $\gamma'H_0$ about the $\vec{z}$ axis.

The second term creates a periodic precession of $\vec{T}_\mu$ peak angular velocity $\gamma'H_p$ and temporal frequency $\Omega$ about the $\vec{z}$ axis.

The third term represents a constant precession of $\vec{T}_\mu$ of angular velocity $\gamma'h_n$ about an axis perpendicular to the $\vec{z}$ axis, said axis rotating with angular velocity $\gamma'H_0$ in the $\vec{x}+j\vec{y}$ Gaussian plane.

These three instantaneous angular velocities add vectorially to a resultant angular velocity, which when integrated over time, creates the locus of $\vec{T}_\mu$ in space.

If $\gamma'h_n \ll \gamma'h_p \ll \Omega \ll \gamma'H_0$, the locus of the unit vector $\vec{T}_\mu$ a serpiqinous line on a unit diameter sphere, said sphere rotating with an angular velocity $\gamma'H_0$ in the $\vec{x}+j\vec{y}$ Gaussian plane (Slichter, op. cit., Ch. 2.4, p. 20)

Output Voltage in Receiver Coil

Define the transverse magnetization $\vec{\mu}_T$ as the projection of the magnetic moment $\vec{\mu}$ on the $\vec{x}+j\vec{y}$ Gaussian plane, which plane is transverse to the $\vec{z}$ axis, such that:

$$\vec{\mu}_T = (\vec{\mu} \sin\theta)e^{j\phi},$$

where $\theta$ is the colatitude of $\vec{\mu}$ with respect to the $\vec{z}$ axis, and $\phi$ is the longitude taken from a zero meridian through the $\vec{z}$ and $j\vec{y}$ axes. The instantaneous angular velocity of $\vec{\mu}_T$ in the $\vec{x}+\vec{y}$ Gaussian plane then is:

$$\vec{\omega}_T = \gamma'h_p\cos(\Omega t) + \gamma'H_0$$

creating a phase incrementation $\phi$ of $\vec{\mu}_T$ at time t of $$\varphi = \int_0^t \vec{\omega}_T \, dt = \frac{\gamma' h_p}{\Omega}\sin(\Omega t) + \gamma' H_0 t.$$

A coil of N turns, with its area vector along the $\vec{x}$ axis will subtend the rotating magnetization of $\vec{\mu}_T$ such that:

$$\mu_c = \mu\sin\theta(\sin\varphi) = (\mu\sin\theta)\sin\left[\frac{\gamma' h_p}{\Omega}\sin(\Omega t) + \gamma' H_0 t\right].$$

By Faraday's law, the voltage induced in the coil is $$V = N\mu_0 \frac{d\mu_c}{dt} = N\mu_0\left((\mu\sin\theta)(\gamma' h_p\cos(\Omega t)+\gamma' H_0)\right)\left(\cos\left[\frac{\gamma' h_p}{\Omega}\sin(\Omega t) + \gamma' H_0 t\right]\right) +$$

$$\sin\left[\frac{\gamma' h_p}{\Omega}\sin(\Omega t) + \gamma' H_0 t\right](\mu\cos\theta)\left(\frac{d\theta}{dt}\right)\right)$$

Since $\frac{d\theta}{dt} \cong \gamma'h_n \ll \gamma'h_p \ll \gamma'H_0$: $V \cong$ $$N(\mu_0\mu\sin\theta)(\gamma' H_0)\left(\cos\left[\frac{\gamma' h_p}{\Omega}\sin(\Omega t) + \gamma' H_0 t\right]\right),$$

where N is the number of turns in the coil, $\mu_0$ is the permeability of free space, $H_0$ is the main magnetic field intensity, $\gamma'$ is the gyromagnetic ratio $\mu_0\gamma$, $h_p$ is the peak magnetic field intensity of the phase modulating field of temporal frequency $\Omega$, and $\theta$ is the colatitude of the magnetic moment (spin) of magnetic field intensity $\mu$.

The Fourier transform of V with respect to time is $$\mathcal{F}V|_\omega = \pi A \sum_{n=-\infty}^{+\infty}\left[J_n\left(\frac{\gamma' h_p}{\Omega}\right)\delta_{[\omega-(\gamma'H_0+n\Omega)]} + J_n\left(\frac{\gamma' h_p}{\Omega}\right)\delta_{[\omega+(\gamma'H_0+n\Omega)]}0\right].$$

where $A=N(\mu_0\mu)(\mu_0H_0)\gamma\sin\theta$. (Poularikas, A. D. ed. "The Transforms and Application Handbook" CRC IEEE Press 1995, op. cit. p. 221, eq. 2.82)

Phase Modulating Field $h_p$

Three voltages are induced in this receiver coil; the first by $h_p$ at a low frequency $\Omega$, the second by $h_n$ of radio frequency (RF) frequency $\gamma'H_0=\gamma\mu_0H_0=\gamma B_0=\omega_0$, and the third by the precession of the magnetic moment $\vec{\mu}$ (spin) consisting of a central frequency $\omega_0$ with an infinite number of sidebands spaced about this central RF Larmor frequency $\omega_0$ at frequency intervals $\Omega$. These sidebands permit adjustment of $h_n$ for the maximum energy transfer condition $\theta=\pi$ since they can be detected in the presence of the Larmor RF frequency $\omega_0$ and the phase modulating low frequency $\Omega$ by rejecting these latter frequencies with circuit filters and/or by detection, heterodyning, and demodulation techniques employed in standard radio receivers. This received first sideband voltage is maximized if the argument of the first sideband is adjusted so that:

$$J_l\left(\frac{\gamma' h_p}{\Omega}\right) \cong J_l(1.8) \cong 0.582$$

(Abramowitz, op. cit. p. 390)
yielding $$\Omega = \frac{\gamma' h_p}{1.8} = \frac{\gamma\mu_0 h_p}{1.8} = \frac{\gamma b_p}{1.8} = \frac{2\pi(42.589\times 10^6)}{1.8}\cdot b_p,$$

then the side band frequency $f_p \cong 23.6\times 10^6 \cdot b_p$ where $2\pi f_p=\Omega$. The peak excursion of the magnetic moment (spin) from the plane containing $H_0$ and orthogonal to $h_n$ is $\pm 1.8$ radians, or $\pm 103$ degrees.

Thus, $\Omega$ and $h_p$ are so defined but are independent of the main magnetic field strength $H_0$ or Larmor frequency $\gamma'H_0=\gamma\mu_0H=\gamma B_0=\omega_0$.

Flow Meter Application

If the magnetic moments (spins) $\vec{\mu}$ of spin density D dwell in a space containing $H_0$ and $h_p$ for a time sufficient to create significant magnetization $\vec{m}=D\vec{\mu}$ (Slichter, op. cit.

Ch. 2.11, p. 51) and then move through a space additionally containing $h_n$ for a dwell time such that nutation occurs through an angle $\theta=\pi$, maximum energy is absorbed by the magnetic moments (spins) $\vec{\mu}$ (Balanis, op. cit. p. 86, eq. 2-81).

A medium (lattice) containing a distribution of magnetic moments $\vec{\mu}$ (spins) traversing a conduit of length $L_1$, in which these magnetic moments are subjected to both a strong magnetic field intensity $\vec{H}_0$ and co-aligned weak component $h_p$, sinusoidally varying with a period $\Omega$, will absorb energy from the magnetic moments by first order kinetics, opposed by random thermal motion, creating a magnetic field intensity $\vec{m}$ such that $$\vec{m} = \vec{\chi}(\vec{H}_0 + \vec{h}_p \cos\Omega t)(1 - e^{-t/T_1}),$$

(where _ denotes both spatial vector and temporal phasor) (Slichter, op. cit., p. 51-59, ch. 2.11), $$\vec{\chi}$$

being the complex susceptibility (Slichter, op. cit., p. 35-39, ch. 2.8), $T_1$ the spin-lattice relaxation (Slichter, op. cit., p. 8, eq. 1.31)

If a subsequent short segment of this conduit of length $L_2$ is additionally subjected to a continuous magnetic field intensity $\vec{h}_n$ orthogonal to $\vec{H}_0$ and rotating in the x, jy Gaussian plane at the Larmor angular velocity $\gamma'H_0 = \gamma\mu_0 H_0 = \gamma B_0 = \omega_0$, the magnetic moments $\vec{\mu}$ (spins) will precess about $\vec{h}_n$ at an angular velocity $\gamma' h_n$ such that:

$$\vec{\omega}_p = \vec{1}_{\mu xy} \vec{h}_n = \frac{d\vec{\theta}}{dt}; \theta = \int_0^\tau \gamma' h_n \, dt; \theta = \gamma' h_n \tau,$$

where $\tau$ is the dwell time of $\vec{\mu}$ in $\vec{h}_n$ and $\theta$ is the colatitude of the plane containing both $\vec{h}_n$ and the magnetic moment with respect to the $\vec{z}$ axis defined by $\vec{H}_0$ (Slichter, op. cit., Ch. 2.4, p. 20). This will create transverse magnetic field intensity $m_T$ such that:

$$m_T = m \sin\theta = \sin\gamma' h_n \tau$$

If the medium (lattice) traverses the conduit at a mean velocity v, the mean distance l traversed in the conduit section of length $L_2$, in time $\tau$ will be $$l = v\tau$$

$$\text{and } m_T = m \sin\left(\frac{\gamma' h_n}{v}l\right),$$

as l increases from zero to $L_2$. If the receiver coil of N turns of width W and length $L_2$ has an area vector $\vec{A}$ that is aligned with the transverse magnetic field intensity $m_T$ along the length $L_2$ of the conduit, then the total magnetic flux $\Phi$ coupled to the receiver coil becomes $$\Phi = N\mu_0 W \int_0^{L_2} m_T \, dl =$$

$$N\mu_0 Wm \int_2^{L_2} \sin\left(\frac{\gamma' h_n}{v}l\right) dl = N\mu_0 Wm \left(\frac{v}{\gamma' h_n}\right) \int_0^{\frac{\gamma' h_n L_2}{v}} \sin x \, dx$$

$$\Phi = N\mu_0 Wm\left(\frac{v}{\gamma' h_n}\right)\left[1 - \cos\left(\frac{\gamma' h_n}{v}L_2\right)\right] = (NWL_2)(\mu_0 m)\frac{1 - \cos\alpha}{\alpha},$$

where $\alpha \equiv \frac{\gamma' h_n}{v}L_2 \cdot \frac{d\Phi}{d\alpha} = (NWL_2)(\mu_0 m)\left(\frac{\sin\alpha}{\alpha} - \frac{1-\cos\alpha}{\alpha^2}\right);$ For maximum $$\Phi, \frac{d\Phi}{d\alpha} = 0,$$

therefore, $\cos\alpha + \alpha\sin\alpha = 1$, and $\alpha = n2\pi$ or $\alpha \cong 2.33$. Then $$v = \frac{\gamma' h'_n}{2.33} L_2.$$

Since, for water protons, $\gamma' = \mu_0\gamma = (4\pi \times 10^{-7})(2\pi)(42.6 \times 10^6)$ then $v \cong (144.5 L_2) h_n$
is the optimum flowmeter equation, with $h_n$ adjusted in each measurement of velocity v for maximum sideband voltage, $J_1(\ ) \cong 0.582 J_0$, at frequency $\omega_0 \pm \Omega$.

Precision $$\frac{d\Phi}{d\alpha} = (NWL_2)(\mu_0 m)\left(\frac{\sin\alpha}{\alpha} - \frac{1-\cos\alpha}{\alpha^2}\right);$$

$$\frac{d^2\Phi}{d\alpha^2} = (NWL_2)(\mu_0 m)\left(\left(\frac{\cos\alpha}{\alpha} - \frac{\sin\alpha}{\alpha^2}\right) - \left(\frac{\sin\alpha}{\alpha^2} - 2\frac{1-\cos\alpha}{\alpha^3}\right)\right) =$$

$$(NWL_2)(\mu_0 m)\left(\frac{\cos\alpha}{\alpha} - 2\frac{\sin\alpha}{\alpha^2} + 2\frac{1-\cos\alpha}{\alpha^3}\right).$$

But $\cos\alpha + \alpha\sin\alpha = 1$, $\cos\alpha = 1 - \alpha\sin\alpha$, for $\frac{d\Phi}{d\alpha} = 0$.

$$\frac{d^2\Phi}{d\alpha^2}\bigg|_{\frac{d\Phi}{d\alpha}=0} = (NWL_2)(\mu_0 m)\left(\frac{1}{a} - \sin a - 2\frac{\sin\alpha}{\alpha^2} + 2\frac{\sin\alpha}{\alpha^2}\right) =$$

$$(NWL_2)(\mu_0 m)\left(\frac{1}{a} - \sin\alpha\right) = (NWL_2)(\mu_0 m)\left(\frac{1}{2.33} - \sin\frac{2.33}{2\pi}(360)\right) =$$

$$(NWL_2)(\mu_0 m)(0.429 - \sin 133.4)\frac{d^2\Phi}{d\alpha^2}\bigg|_{\frac{d\Phi}{d\alpha}=0} =$$

$$(NWL_2)(\mu_0 m)(-0.298).$$

The rate of change of slope of output voltage about the maximum value of $\alpha$ is proportional to the magnetization $\vec{m}$ and the receiver coil area $WL_2$.

Scale Restrictions on $L_2$, $f_p$ by Range of Velocity v

The Fourier transform analysis of the receiver coil voltage, as expressed, applies strictly to a non-bounded function. The observation of this voltage is truncated in time by the dwell time $\tau_2$ of the magnetic moments $\vec{\mu}$ (spins) in the short conduit segment of length $L_2$. This truncation is the mathematical equivalent of multiplication by a unit pulse function of duration $T_2$, creating convolution of the Fourier transform by a sinc function (Poularikas, op. cit., p. 6, eq. 4, 6, and p. 204, Table 2.4) broadening each element of the sidebands and degrading signal-to-noise ratio, since the minimum noise power is proportional to sideband width.

This is obviated by making the frequency $\Omega$ of the phase modulating magnetic field intensity $h_p$ sufficiently large so that $$\Omega = 2\Omega f_p \gg \frac{2\pi}{\tau_2}, f_p \gg \frac{1}{\tau_2}$$

noting $f_p \cong 23.6 \times 10^6 \cdot b_p$ and $vL_2 = \tau_2$, the transit time through $L_2$.

Since there are inhomogeneties in the magnetic field intensities ambient to each magnetic moment $\vec{\mu}$ (spin) and each such magnetic moment is subject to random displacement by both passive diffusion and active fluid turbulence, there is a progressive loss of coherence of the magnetic moments created by random phase incrementations $d\varphi$ during transit of the medium (lattice) through the short receiver section of the conduit of length $L_2$. These are the $T_2^*$ effects progressively diminishing coherent magnetization along the segment of length $L_2$ of the conduit by first order kinetics (Slichter, op. cit., p. 34, 35).

Thus, $\tau_2 \ll T_2^*$ to preserve signal strength and, therefore, precision.

Noise Budget
1) Major Components:
   a) Main Magnet plus RF shielding
      i) Resistive—D.C. power supply and hot coil can be source of RF noise mutually coupled to receiver coil.
      ii) Permanent—Thermal noise capacitively coupled to receiver coil.
      iii) Superconducting—minimal noise.
      iv) Hybrid—as above.
   b) Phase Modulating Coil and ELF Power Supply
      i) Stable C. W. ELF (1-10 kHz) Power Supply must be monochromatic and with constant current output.
      ii) Phase Modulating Coil of low resistance to reduce thermal noise mutually coupled to receiver coil.
   c) RF Transmitter Coil and Adjustable RF Power Supply
      i) RF Transmitter Coil of low resistance to reduce thermal noise mutually coupled to receiver coil.
      ii) Monochromatic RF Power Supply auto-tuned to the slightly variable, Larmor frequency.
   d) RF Receiver Coil and RF Receiver Circuit.
      i) RF Receiver Coil of low resistance forming a very high Q resonant circuit.
      ii) RF Receiver Circuit impedance matched to RF Receiver coil with cross-correlation to RF Power Supply frequency to extract received signal from received noise.
   e) Controller Circuit Controls RF Transmitter Power Supply Larmor frequency and measured value of current output to RF Transmitter Coil to achieve maximum RF Receiver Circuit output.
2) Schedule of Major Components:
   a) Main Magnet
   b) Phase Modulating Coil
   c) Phase Modulating Coil Power Supply, ELF (1-10 kHz)
   d) RF Transmitter Coil
   e) RF Transmitter Coil Power Supply, Larmor frequency
   f) RF Receiver Coil
   g) RF Receiver Circuit
   h) Controller Circuit
   i) Conduit and Mechanical Supports and Seals
3) Noise Contributions in Order of Severity:
   a) The two power supplies should be monochromatic dedicated circuitry.
   b) The three coils must be high Q, low resistance, low noise.
   c) The receiver coil must be a narrow passband resonant circuit that does not oscillate when impedance matched to the receiver.

Signal Strength

Signal strength varies as less than the square of the Main Magnet field strength, directly with length $L_1$ of the Main Magnet, and linearly with the area of the Receiver Coil, the latter being a function of conduit diameter. Field homogeneity in the receiver section $L_2$ is a function of the length of the Main Magnet before and after $L_2$. The dwell time $T_1$ in the magnetizing section of length $L_1$ must be a significant fraction of the spin-lattice relaxation time of the moving material $T_1$.

Rangeability

The Range of Velocity v should be converted to dwell times $\tau_1$ and $\tau_2$ for lengths $L_1$ and $L_2$, for each flow range application, and compared to $T_1$ spin-lattice and $T_2^*$ spin-spin relaxation times for each class of material measured.

With this background, a flow measurement device implementing these principles can be described.

Figures 1A, 1B:
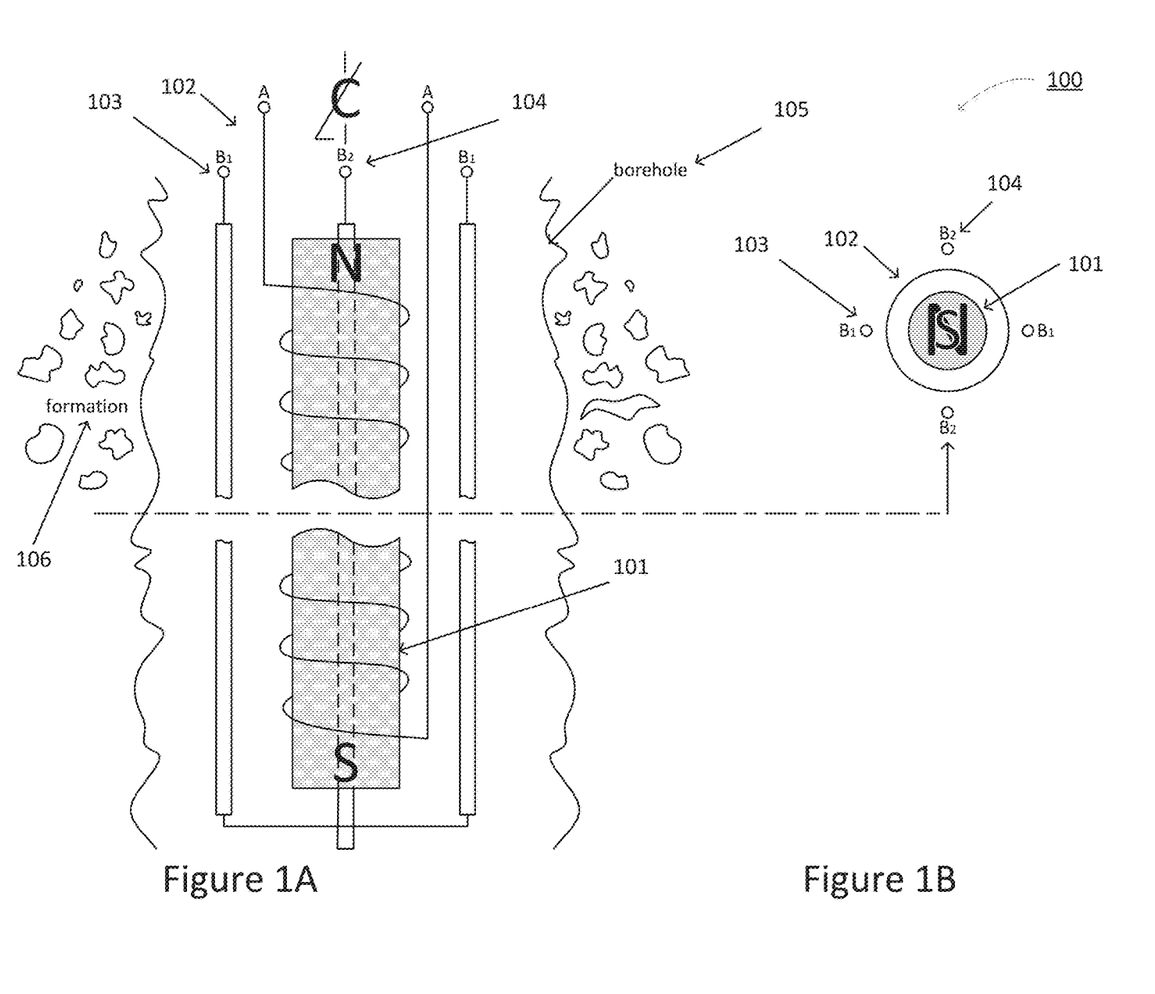
FIGS. 1A and 1B show a cross-sectional side view and top view of an example embodiment of a flow measurement device.

FIGS. 1A and 1B show a cross-sectional side view and top view, respectively, of an example embodiment of a flow measurement device 100. The flow measurement device 100 includes a magnet 101 having north and south poles, an electromagnet 102, and radio frequency ("RF") coils 103 and 104. The flow measurement device 100 is configured to insert into a borehole 105 of an earth formation 106.

The flow measurement device 100 can include a magnet 101. The magnet 101 can generate a static magnetic field around the flow measurement device 100 that is generally solenoidal in shape. The strength of the static magnetic field is not critical to the function of the flow measurement device 100, but can generally be in the range of several Gauss to several Tesla. The strength of the static magnetic field generated by magnet 101 can decrease in strength peripherally from the magnet. The magnet 101 can include a permanent magnet. The magnet 101 can alternatively include a conventional or superconducting electromagnet. The magnet 101 can be of any size or shape appropriate to the dimensions of the borehole and the flow measurement application for which it will be used, including a long or short cylindrical shape.

The flow measurement device 100 can include an electromagnet 102. The electromagnet 102 can be configured to generate a time varying magnetic field around the flow measurement device 100 that is generally solenoidal in shape. The electromagnet 102 can be of any type suitable for generating a solenoidal magnetic field of roughly the same relative distribution as the static magnetic field. The electromagnet 102 can take the shape of a helical coil surrounding the magnet 101. The strength of the time varying magnetic field generated by the electromagnet 102 can vary linearly with the application of a time varying current through the electromagnet 102. The strength of the time varying magnetic field generated by the electromagnet 102 can be relatively weak compared to the strength of the static magnetic field; for example, a fraction of a Gauss to several Gauss. The frequency of the time varying magnetic field generated by the electromagnet 102 can be relatively low in frequency compared to the frequency of the RF magnetic field generated by the RF coils 103 and 104.

The flow measurement device 100 can include radio frequency ("RF") coils 103 and 104. The RF coils can be configured to generate a time varying magnetic field $h_1$ transverse to the $H_0$ static solenoidal magnetic field generated by the magnet 101 and electromagnet 102. The RF coils 103 and 104 can be a single coil or made up of more than two coils. The RF coils 103 and 104 can be a single coil configured to both transmit and receive time varying magnetic fields. Alternatively, separate RF coils 103 and 104 can be employed as a transmit coil and a receiving coil, respectively. The RF coils 103 and 104 can be of a birdcage or quadrature design, or any other coil, cage, or antenna structure suitable for directing an RF magnetic field outward from the flow measurement device 100. In one embodiment, the RF coils 103 and 104 comprise a transmitting birdcage coil disposed around the magnet and configured to generate the RF magnetic field, and a receiving birdcage coil disposed around the magnet and configured to output the received signal. In another embodiment, the RF coils 103 and 104 could comprise a first birdcage coil disposed around the magnet and configured to operate at a first frequency, and a second birdcage coil disposed around the magnet and configured to operate at a second frequency. The RF coils 103 and 104 can be tuned to resonate at the desired frequency of operation. Tuning of the RF coils 103 and 104 can be accomplished mechanically or electrically by adjusting a component such as a variable capacitor or inductor. An example of an electrically tunable capacitor is a varicap or varactor diode. An example of a mechanically tunable capacitor is a variable or tuning capacitor. The RF coils 103 and 104 can have a high quality factor ("Q") for improved efficiency of transmission and receipt of time varying magnetic fields. The RF coils 103 and 104 can be adjusted by these or other methods to generate a time varying $h_1$ magnetic field rotating at the Larmor frequency $\omega_0 = \gamma h_0$ corresponding to the $H_0$ static solenoidal magnetic field intensity $h_0$ in a region of interest around the flow measurement device 100. The region of interest can take the shape of a barrel shaped prolate or oblate ellipsoidal surface having a finite thickness generated about the centerline of the flow measuring device 100. The RF coils 103 and 104 can be configured to output a received signal induced by the magnetic field about the RF coils 103 and 104.

Multiple RF coils 103 an 104 can be employed to measure the relative abundance of two different spin species; for example, detection and measurement of both $^1H$ and $^{13}C$ by the same flow measurement device 100. Exciting RF coils 103 and 104 with frequencies selected for two different spin species permits implementation of the nuclear Overhauser effect yielding the mean dwell time of, e. g., $^1H$ and $^{13}C$, thereby implementing a multiphase "cut meter" or wireline logging modality. Such a system may be valuable, for example, for measuring the relative abundance of hydrocarbons versus brine in the region surrounding the flow measurement apparatus. Such information can be valuable when searching for hydrocarbon deposits.

In operation, the magnet 101 and electromagnet 102 can create a strong solenoidal field with a weak slowly time varying component in the borehole 105 and in the surrounding disturbed and undisturbed earth formation 106. The RF coils 102 and 103 can create an adjustable RF magnetic field essentially orthogonal to the solenoidal field. The RF magnetic field rotates at the Larmor frequency and causes the spins to nutate with increasing angle with respect to the strong magnetic field, permitting reception of a received signal induced by a magnetic field created by the nutating spins at sideband frequencies slightly displaced from the Larmor frequency. Selecting the Larmor frequency selects the depth of investigation, where the depth of investigation represents the distance from the flow measurement device 100 to the region of interest of spin activation about the flow measurement device. That is, for a given strength of the static solenoidal magnetic field $H_0$, adjusting the frequency of the RF magnetic field generated by the RF coils 103 and 104 controls at what distance from the flow measurement device 100 spins will be affected. An RF magnetic field having a higher frequency will activate spins relatively closer to the flow measurement device 100, and an RF magnetic field having a lower frequency will activate spins relatively further from the flow measurement device 100. The strength of the slowly varying component of the solenoidal field is adjusted for optimum signal reception of the first sideband frequencies from the depth of investigation.

The conditions generated by the flow measurement device 100 create both nutation, with increasing flip angle, and periodic phase modulation of the rotational Larmor frequency of the spins. The received signal then induced in the RF coils 103 and 104 is sinusoidal with slowly varying frequency whose Fourier transform yields a central Larmor frequency and discrete side bands displaced by the phase modulation frequency. These side bands can then be detected in the presence of the strong Larmor excitation frequency field by means known in the art including heterodyne frequency shift, quadrature detection, and cross correlation in a lock-in amplifier. Adjusting the strength of the Larmor excitation frequency field for maximum received signal yields a known function of the mean dwell time of the spins at the depth of investigation. This permits measurement of the peripheral velocity of flow in the formation or the linear velocity of flow within the borehole, depending on the selected depth of investigation.

In use, the Larmor $\omega_0$ for the desired depth of investigation can be set—this can be the frequency of the signal transmitted by the RF coils 103 and 104, and hence the frequency of the RF magnetic field. The current in electromagnet 102 can be adjusted to maximize the value of the first side band about the Larmor frequency from the received signal induced in the RF coils 103 and 104. The optimum current can be set experimentally for the given depth of investigation. The exact optimum current for the exact maximum signal need not be established precisely, but in general a greater received signal can yield better measurements. To estimate peripheral velocity of flow, the magnitude of the current in the RF coils 103 and 104 can be set for maximum received signal. The magnitude of the RF current is a linear function of the mean dwell time of the spins in the depth of investigation. Extrapolating from the mean dwell time of spins through the region of interest can yield the average velocity of those spins either through the formation 106 or linearly along the borehole 105.

Figure 2:
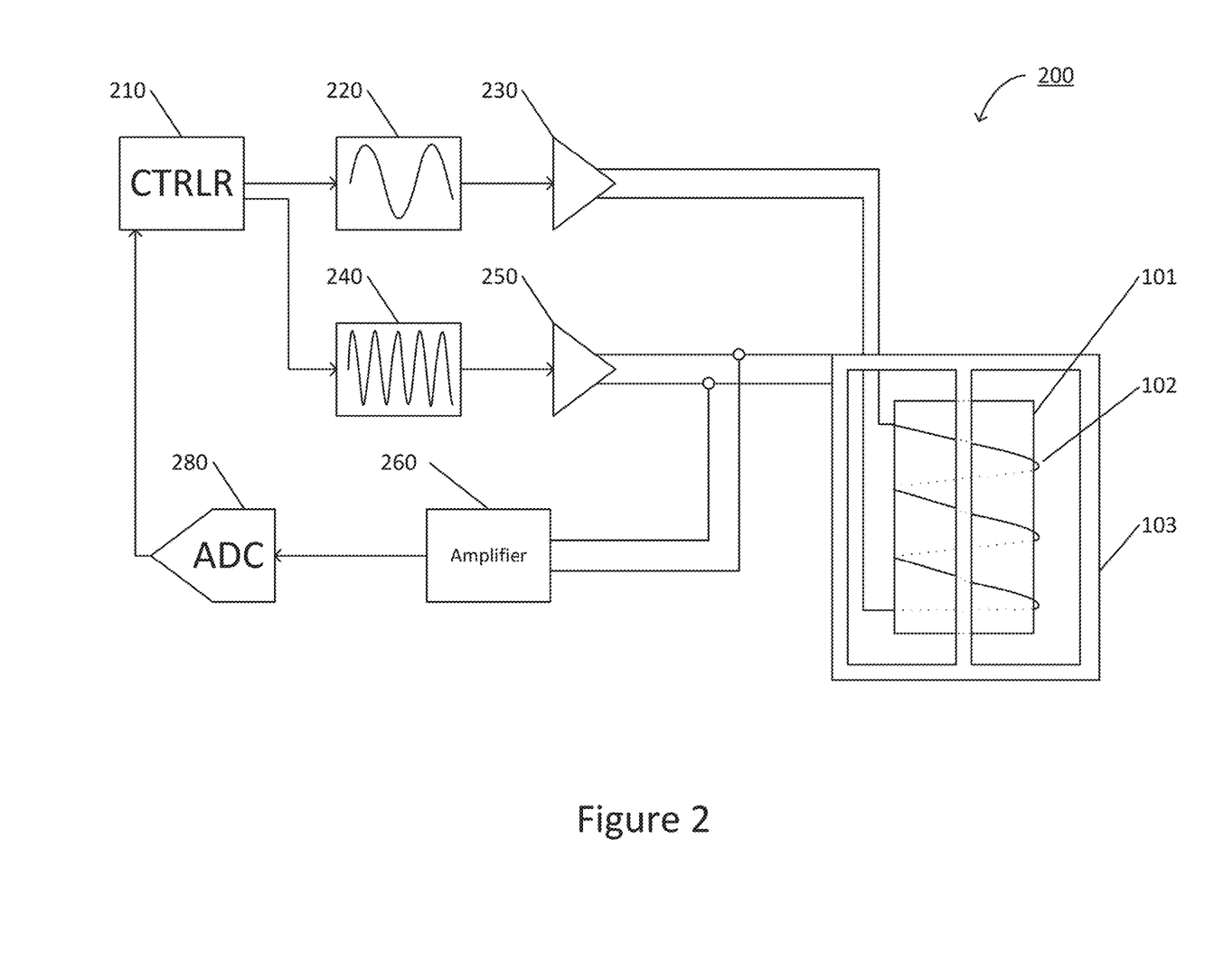
FIG. 2 shows a simplified functional block diagram of an example embodiment of a flow measurement device.

FIG. 2 shows a simplified functional block diagram of an example embodiment of a flow measurement device 200. The flow measurement device 200 includes magnet 101, electromagnet 102, and RF coil 103 described previously. The flow measurement device 200 can include a controller 210, a function generator 220, an amplifier 230, a function generator 240, an amplifier 250, an amplifier 260, and an analog-to-digital convertor ("ADC") 280.

The flow measurement device 200 can include a controller 210. The controller 210 can comprise a microcontroller, a microprocessor, an application-specific integrated circuit, a field-programmable gate array, CPU, personal computer, or any other device capable of controlling the elements of the flow measurement device. The controller 210 can be capable of storing and performing, in conjunction with the remaining components of the flow measurement device 200, steps of a method of measuring flow in and around a borehole. The controller 210 can have outputs suitable for controlling function generator 220 and function generator 240. The controller 210 can control the function generators 220 and 240 via analog or digital outputs. Alternatively, the controller 210 can include function generators 220 and 240 within its own hardware or software. In such cases, the controller 210 can have analog outputs corresponding to the outputs of function generators 220 and 240. Those outputs can couple to amplifier 230 and amplifier 250, respectively. The outputs of function generators 220 and 240 can be analog or digital electrical signals including square wave, sinusoidal wave, and other periodic functions suitable for driving the electromagnet 102 and RF coil 103 via amplifiers 230 and 250, respectively.

The output of function generator 220 can be amplified by amplifier 230 to a voltage or current sufficient to drive the electromagnet 102 to generate a sufficiently strong time varying solenoidal magnetic field. The output of function generator 220 can be a sine wave appropriate for causing the necessary spin phase modulation in the region of interest. If the electromagnet 102 is driven by amplifier 230 in a resonant condition, it may be appropriate to drive it with a square wave or other periodic waveform as the resonator will bandwidth limit the current flowing in electromagnet 102, ultimately resulting in a sinusoidal current in the electromagnet 102.

The output of function generator 240 can be amplified by amplifier 250 to a voltage or current sufficient to drive the RF coil 103 to generate a sufficiently strong RF magnetic field. As with the function generator 220 and amplifier 230 driving the electromagnet 102, the output of function generator 240 can be a sine wave appropriate for causing the necessary spin nutation in the region of interest. If the RF coil 103 is driven by amplifier 250 in a resonant condition, it may be appropriate to drive it with a square wave or other periodic waveform as the resonator will bandwidth limit the current flowing in RF coil 103, ultimately resulting in a sinusoidal current in the RF coil 103.

The flow measurement device 200 can include an amplifier 260 and analog-to-digital convertor ("ADC") 280 for receiving the received signal induced by a magnetic field around the RF coil 103. As described above, the received signal induced in the RF coil 103 is sinusoidal with slowly varying frequency whose Fourier transform yields a central Larmor frequency and discrete side bands displaced by the phase modulation frequency. These side bands can then be detected in the presence of the strong Larmor excitation frequency field by means known in the art including heterodyne frequency shift, quadrature detection, and cross correlation in a lock-in amplifier. Thus, in some implementations, the amplifier 260 can include a lock-in amplifier. The amplifier 260 can isolate and amplify the first side band detected by the RF coil 103. In using this technique, the bandwidth of the detected signal can be very small to infinitesimal, reducing the noise in the measurement. The ADC 280 can receive the detected first sidebands and quantize them into digital values for use by the controller 210. In some implementations, the ADC 280 can be included in the software or hardware of the controller 210. Alternatively, the ADC 280 can be a separate component. The ADC 280 can quantize the detected first sidebands for use by the controller 210 for setting the parameters of operation of the flow measurement device 200 including the magnitude of the time varying current applied to the electromagnet 102 and the magnitude of the RF current applied to the RF coil 103. The ADC 280 can quantize the detected first sidebands for use by the controller 210 in calculating the dwell time of spins within the region of interest. The controller 210 can calculate, based on the detected first sidebands and the parameters of operation of the flow measurement device 200, the dwell time of spins within the region of interest. The controller 210 can calculate, based on the dwell time of spins within the region of interest, the flow velocity through the region of interest around the flow measurement device.

The controller 210 can calculate the flow velocity based on the received signal. To calculate the flow velocity, controller 210 can select the Larmor frequency to correspond to the region of interest around the flow measurement device. The controller 210 can adjust the magnitude of the time varying current in the electromagnet 102 to maximize the magnitude of the first side band about the Larmor frequency of the received signal. The time varying solenoidal magnetic field generated by the electromagnet 102 will cause the spins within the region of interest to emit an RF magnetic field that can be sinusoidal with slowly varying frequency whose Fourier transform yields a central Larmor frequency and discrete side bands displaced by the phase modulation frequency. These side bands can then be detected in the presence of the strong Larmor excitation frequency field by employing, for example, heterodyne frequency shift, quadrature detection, and cross correlation in a lock-in amplifier. The controller 210 can adjust a magnitude of an RF current applied to the RF coil 103 to maximize the received signal. The magnitude of the RF current applied to the RF coil 103 can exhibit a linear relationship with the mean dwell time of spins in the depth of investigation. The controller 210 can calculate the mean dwell time of spins moving through the region of interest based on the magnitude of the RF current. The controller 210 can, based on the mean dwell time of the spins, calculate the average velocity of those spins through the formation 106 or linearly along the borehole 105.

Figure 3:
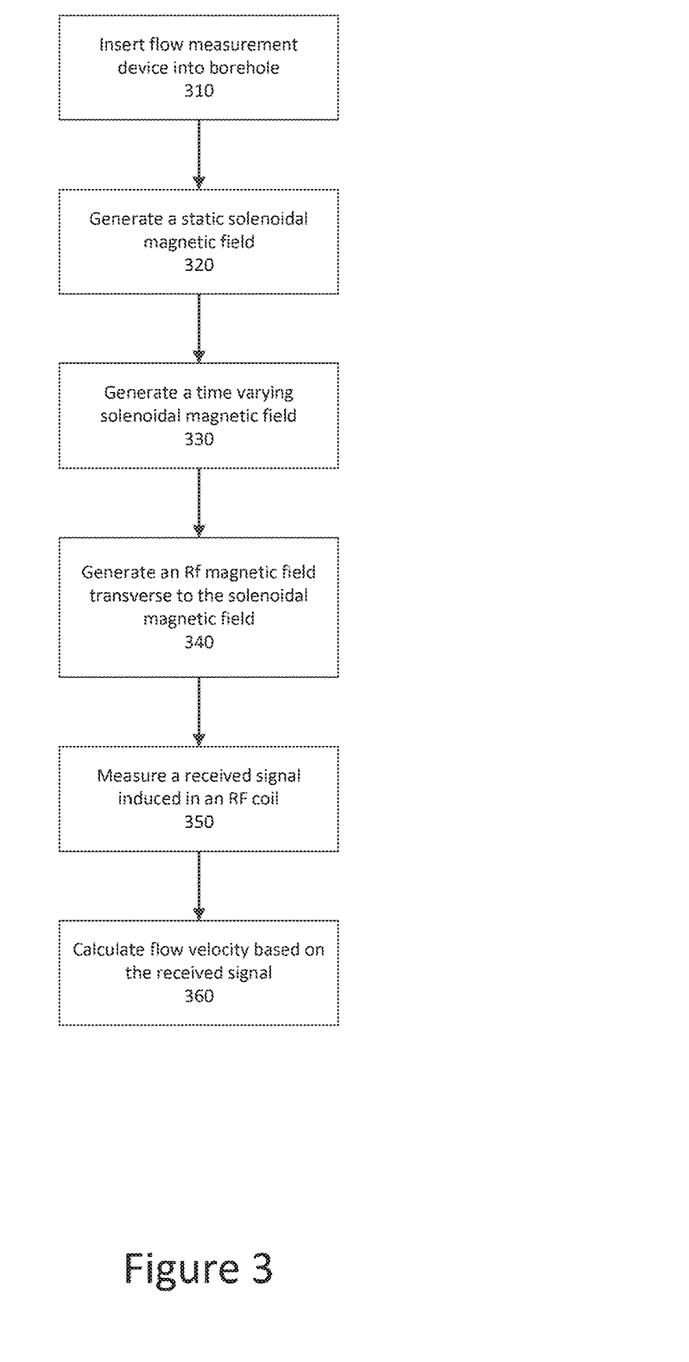
FIG. 3 shows a flow diagram of an example method for measuring flow in or around a borehole in an earth formation.

FIG. 3 shows a flow diagram of an example method for measuring flow in or around a borehole in an earth formation. The method can include inserting a flow measurement device into a borehole (STEP 310). The method can include generating a static solenoidal magnetic field (STEP 320). The method can include generating a time varying solenoidal magnetic field (STEP 330). The method can include generating an RF magnetic field transverse to the solenoidal magnetic fields (STEP 340). The method can include measuring a received signal induced in an RF coil (STEP 350). The method can include calculating the flow velocity based on the received signal (STEP 360).

The method can include inserting a flow measurement device into a borehole (STEP 310). The flow measurement device can be inserted into a borehole or other feature. The borehole can be manmade or a natural feature. The borehole can represent a pipe, tunnel, culvert, canal, fissure, crack, well, or any other type of opening or conduit. The flow measurement device can perform measurements of flow in the borehole itself, or in some connected feature such as a chamber, pocket, tank, aquifer, cavern, reservoir, or the like.

The method can include generating a static solenoidal magnetic field (STEP 320). The static solenoidal magnetic field $H_0$ can be generated by any type of electrical or permanent magnet as described previously. The field intensity $h_0$ of the solenoidal magnetic field can decrease in strength peripherally from the magnet 101. The Larmor frequency of particular spins in any region around the magnet 101 will depend on the intensity of the solenoidal magnetic field in that region ($\omega_0 = \gamma h_0$).

The method can include generating a time varying solenoidal magnetic field (STEP 330). The time varying solenoidal magnetic field can be generated by applying a corresponding time varying current to the electromagnet 102. The strength of the time varying solenoidal magnetic field can vary linearly with the magnitude of the current applied to the electromagnet 102. The strength of the time varying magnetic field can decrease with distance from the electromagnet 102. The magnitude of the time varying current in electromagnet 102 can be adjusted to maximize the value of the first side band about the Larmor frequency from the received signal induced in the RF coils 103 and 104. The optimum current can be set experimentally for the given depth of investigation. The exact optimum current for the exact maximum signal need not be established precisely, but in general a greater received signal can yield better measurements.

The method can include generating an RF magnetic field transverse to the solenoidal magnetic fields (STEP 340). The RF coils 103 and 104 can generate the RF magnetic field. The frequency of the RF magnetic field can be set to the Larmor $\omega_0$ for the desired spins at the desired depth of investigation. The Larmor frequency will apply to spins within a region of interest approximating a surface of a prolate or oblate spheroid with a finite thickness about the magnet 101. The region of interest can have a relatively narrow slice thickness on the order of millimeters, depending on the gradient of the static magnetic field and the bandwidth of the RF magnetic field. The field intensity $h_0$ can be roughly constant across this region of interest. The exact shape of the region can depend on the shape of the magnet 101.

The method can include measuring a received signal induced in an RF coil (STEP 350). As described above, the flow measurement device 100 can include a combined transmit and receive RF coil, or separate transmit and receive RF coils. To estimate peripheral velocity of flow, the magnitude of the current in the RF coils 103 and 104, as applied in STEP 340, can be set for maximum received signal in STEP 350. The time varying solenoidal magnetic field applied at STEP 330 will cause the spins within the region of interest to emit an RF magnetic field that can be sinusoidal with slowly varying frequency whose Fourier transform yields a central Larmor frequency and discrete side bands displaced by the phase modulation frequency. These side bands can then be detected in the presence of the strong Larmor excitation frequency field by employing, for example, heterodyne frequency shift, quadrature detection, and cross correlation in a lock-in amplifier as described above.

The method can include calculating the flow velocity based on the received signal (STEP 360). To estimate peripheral velocity of flow, the magnitude of the current in the RF coils 103 and 104 applied in STEP 340 can be set to maximize the magnitude of the first sideband about the Larmor frequency in the received signal. The magnitude of the RF current can display a linear relationship with the mean dwell time of the spins in the depth of investigation. The mean dwell time of spins moving through the region of interest can be calculated based on the magnitude of the RF current. The average velocity of those spins either through the formation 106 or linearly along the borehole 105 can be calculated from the mean dwell time of the spins.

The foregoing disclosure is equally applicable to nuclear and electron magnetic resonance. Furthermore, the measurement of velocity by the device described in this disclosure is applicable not only to liquid or gas, but to flow of other fluid materials, such as mixtures, slurries, aggregates, blowing particles, viscous plastics as well as to the flow of solid materials.

Preferred embodiments of the invention have now been described. It will be appreciated by those skilled in the art that such embodiments are intended to exemplify the invention. Various other embodiments of the invention will be apparent, which fall within the spirit and scope of the invention.

The invention claimed is:

1. A flow measurement device for measuring flow in a region of interest in or around a borehole of an earth formation, comprising:
   a magnet configured to generate a static solenoidal magnetic field with a field intensity that decreases in strength peripherally from the magnet;
   an electromagnet disposed around the magnet and configured to generate a time varying solenoidal magnetic field; and
   a radio frequency (RF) coil disposed around the magnet and configured to:
      generate an RF magnetic field transverse to the static solenoidal magnetic field and rotating at the Larmor radio frequency corresponding to the field intensity in the region of interest around the flow measurement device; and
      output a received signal, the received signal induced by a magnetic field around the RF coil.

2. The flow measurement device of claim 1, wherein the electromagnet is a helical coil disposed around the magnet.

3. The flow measurement device of claim 1, wherein the RF coil comprises a birdcage coil disposed around the magnet.

4. The flow measurement device of claim 1, wherein the RF coil comprises a first birdcage coil disposed around the magnet and configured to operate at a first frequency, and a second birdcage coil disposed around the magnet and configured to operate at a second frequency.

5. The flow measurement device of claim 1, wherein the RF coil comprises a transmitting birdcage coil disposed around the magnet and configured to generate the RF magnetic field, and a receiving birdcage coil disposed around the magnet and configured to output the received signal.

6. The flow measurement device of claim 1, wherein the RF coil comprises a quadrature coil.

7. The flow measurement device of claim 1, wherein the region of interest around the flow measurement device is a surface of a prolate or oblate spheroid having a finite thickness.

8. The flow measurement device of claim 1, further comprising a controller configured to calculate a flow velocity through the region of interest around the flow measurement device based on the received signal.

9. The flow measurement device of claim 8, wherein the controller is further configured to:
   select the Larmor frequency to correspond to the region of interest around the flow measurement device;
   adjust a magnitude of a time varying current applied to the electromagnet to maximize a magnitude of a first side band of the received signal; and
   adjust a magnitude of an RF current applied to the RF coil to maximize the received signal.

10. The flow measurement device of claim 9, wherein the controller is further configured to:
   calculate a mean dwell time of spins in the region of interest around the flow measurement device based on the magnitude of the RF current applied to the RF coil; and calculate the flow velocity through the region of interest around the flow measurement device based on the received signal.

11. A method of measuring flow in or around a region of interest in a borehole in an earth formation, comprising:
   inserting a flow measurement device into the borehole in the earth formation, the flow measurement device comprising a magnet, an electromagnet disposed around the magnet, and a radio frequency (RF) coil disposed around the magnet;
   generating, using the magnet, a static solenoidal magnetic field, wherein the static solenoidal magnetic field has a field intensity that decreases in strength peripherally from the magnet;
   generating, using the electromagnet, a time varying solenoidal magnetic field;
   generating, using the RF coil, an RF magnetic field transverse to the static solenoidal magnetic field and rotating at a Larmor radio frequency corresponding to the field intensity in the region of interest around the flow measurement device; and
   receiving a received signal induced in the RF coil by a magnetic field around the RF coil.

12. The method of claim 11, wherein the electromagnet is a helical coil disposed around the magnet.

13. The method of claim 11, wherein the RF coil comprises a birdcage coil disposed around the magnet.

14. The method of claim 11, wherein the RF coil comprises a first birdcage coil disposed around the magnet and configured to operate at a first frequency, and a second birdcage coil disposed around the magnet and configured to operate at a second frequency.

15. The method of claim 11, wherein the RF coil comprises a transmitting birdcage coil disposed around the magnet and configured to generate the RF magnetic field, and a receiving birdcage coil disposed around the magnet and configured to output the received signal.

16. The method of claim 11, wherein the RF coil comprises a quadrature coil.

17. The method of claim 11, wherein the region of interest around the flow measurement device is a surface of a prolate or oblate spheroid having a finite thickness.

18. The method of claim 11, further comprising calculating a flow velocity through the region of interest around the flow measurement device based on the received signal.

19. The method of claim 18, further comprising:
   selecting the Larmor frequency to correspond to the region of interest around the flow measurement device;
   adjusting a magnitude of a time varying current applied to the electromagnet to maximize a magnitude of a first side band of the received signal; and
   adjusting a magnitude of an RF current applied to the RF coil to maximize the received signal.

20. The method of claim 19, further comprising:
   calculating a mean dwell time of spins in the region of interest around the flow measurement device based on the magnitude of the RF current applied to the RF coil; and
   calculating the flow velocity through the region of interest around the flow measurement device based on the received signal.

* * * * *